United States Patent [19]

Drauz et al.

[11] Patent Number: 5,707,837
[45] Date of Patent: Jan. 13, 1998

[54] METHOD OF PRODUCING (R)-TERTIARY LEUCINE

[75] Inventors: Karlheinz Drauz, Freigericht; Andreas Bommarius, Frankfurt; Matthias Kottenhahn, Freigericht, all of Germany

[73] Assignee: Degussa Aktiengesellschaft, Frankfurt, Germany

[21] Appl. No.: 696,805

[22] Filed: Aug. 9, 1996

[30] Foreign Application Priority Data

Aug. 9, 1995 [DE] Germany ............... 195 29 211.1

[51] Int. Cl.$^6$ .............................. C12P 13/04; C12P 13/06
[52] U.S. Cl. ................................. 435/116; 435/106
[58] Field of Search ............................... 435/116, 106

[56] References Cited

U.S. PATENT DOCUMENTS

| | | |
|---|---|---|
| 4,744,990 | 5/1988 | Bragdon et al. ............ 426/2 |
| 4,871,552 | 10/1989 | Bragdon et al. ............ 426/2 |
| 5,516,660 | 5/1996 | Wagner et al. ............ 435/106 |

FOREIGN PATENT DOCUMENTS

| | | |
|---|---|---|
| 0 141 223 | 5/1985 | Germany . |
| 7222593 | 8/1995 | Japan . |
| 9 001 680 | 2/1992 | Netherlands . |

OTHER PUBLICATIONS

Bommarius, et al., Tetrahedron: Asymmetry, (1995) "Synthesis and Use of Enantiomerically Pure Tert-Leucine", pp. 2853–2888.

*Primary Examiner*—Leon B. Lankford, Jr.
*Assistant Examiner*—Christopher R. Tate
*Attorney, Agent, or Firm*—Cushman Darby & Cushman IP Group of Pillsbury Madison & Sutro LLP

[57] ABSTRACT

A method is disclosed by which N-carbamoyl-(R)-tert.-leucine is obtained from tert-butyl hydantoin by means of an (R)-specific hydantoinase, in which N-carbamoyl-(R)-tert.-leucine is converted by reaction with nitrite or an (R)-carbamoylase to (R)-tert-leucine.

7 Claims, No Drawings

METHOD OF PRODUCING (R)-TERTIARY LEUCINE

This application is based on application no. 195 29 211.1 filed in Germany on Aug. 9, 1995, the content of which is incorporated herein by reference.

BACKGROUND OF THE INVENTION

1. Field of the Invention

The invention relates to a method of producing (R)-tertiary leucine. (R)-tertiary leucine is significant in asymmetric synthesis, where it serves, especially in reduced form as (R)-tert-leucinol, for the efficient induction of asymmetry in many chemical reactions (see A. S. Bommarius et al., Tetrahedron Asymmetry, 1995).

2. Prior Art

In contrast to the enantiomeric form, (S)-tertiary leucine, which is accessible, for example, by enzymatic, reductive amination [(1) C. Wandrey and B. Bossow, Biotechnol. Bioind. 1986, volume 3, pp. 8–13, and (2) V. Kragl et al., Chem. Ing. Techn. 1992, volume 64, pp. 499–509)], (R)-tertiary leucine has been difficult to access up to the present. Thus, for example, an acylase reacts only extremely slowly with N-acetyl-(R,S)-tert leucine (see H. K. Chenault, J. Dahmer and G. M. Whitesides, J. Amer. Chem. Soc. 1989, 111, 6354–64), so that the isolation of (R)-tertiary leucine from the non-hydrolysed acetyl-(R)-tert-leucine is very expensive and proceeds with a low space/time yield.

Accordingly, the invention addresses the problem of making available a novel method for producing (R)-tertiary leucine which does not have the above-named disadvantages.

SUMMARY OF THE INVENTION

This problem is solved by a process wherein tertiary butyl hydantoin is reacted with an (R)-hydantoinase and then the N-carbamoyl-R-tertiary leucine produced is allowed to react further to (R)-tertiary leucine either by another enzyme reaction with carbamoylase or by compounding with nitrite.

(R)-hydantoinases are known basically from: a) IT 1109506, 1978; b) R. Olivieri, E. Fascetti, L. Angelini and L. Degen, Enzyme and Microbial Technology, 1979, volume 1, pp. 201–204; c) H. Yamada et al., J. Ferment. Technol. 1978, 56, 484 ff.; d) C. Syldatk et al., J. Biotechnol. 1990, 14, 345 ff; e) O. Keil, M. Schneider and J. P. Razor, Tetrahedron Asymmetry, 1995, 6, 1257–60; and f) EP 0,643, 133 A2.

It was surprisingly found that tert. butylhydantoin from the (R)-hydantoinase from *Escherichia coli* is completely reacted to N-carbamoyl-(R)-tertiary leucine. The further reaction to (R)-tertiary leucine can take place with the aid of another enzyme reaction with a carbamoylase or by a further reaction in the presence of nitrite.

DETAILED DESCRIPTION OF PREFERRED EMBODIMENTS OF THE INVENTION

In the method of the invention (R,S)-tert. butyl hydantoin or (S)-tert. butyl hydantoin is reacted thereby in a suitable solvent, such as water, at pH values between 6.0 and 11, preferably between 7.5 and 10.5, especially preferably between 8.5 and 10, and at a temperature between 0° C. and 80° C., preferably between 25° C. and 60° C., especially preferably between 40° C. and 50° C., with an (R)-specific hydantoinase with the optional addition of auxiliary agents such as metal ions, e.g. $Mn^{2+}$ ions, at a constant pH. After the end of the reaction the product produced, N-carbamoyl-(R)-tertiary leucine, is separated from the biocatalyst by filtration (in the case of immobilized enzymes) or by ultrafiltration (in the case of soluble enzymes). In the next step N-carbamoyl-(R)-tertiary leucine is reacted in a known manner (C. Syldatk, A. Läufer, R. Müller and H. Höke, Adr. Biochem. Eng./Biotechnol. 1990, vol. 41, p. 29 ff and literature cited therein) with the aid of a D-carbamoylase to (R)-tertiary leucine, or N-carbamoyl-(R)-tertiary leucine is decarbamoylized in an acidic, aqueous solution, such as HCl-acidic-aqueous solution, at temperatures between 0° and 30° C. by the addition of a nitrite, such as sodium nitrite, and the resultant product is freed of salt by ion exchange chromatography. The eluate is clarified with activated carbon, the (R)-tertiary leucine produced being precipitated by evaporating the solvent to low bulk and drying.

Advantageously, both (R,S)-tertiary butylhydantoin and (S)-tertiary butyl hydantoin can be used as the initial substance in the method of the invention since the hydantoins used racemize under the reaction conditions so that (R)-tertiary butyl hydantoin reacted to N-carbamoyl-(R)-tertiary leucine is reproduced by racemization and the conversion can thus be up to 100%.

The (R)-specific hydantoinases used can be present both in soluble form as well as immobilized. R-hydantoinases such as those described in citations e) and f) supra, are especially preferred.

The invention is explained in further detail in the following examples, but is not limited to them.

Production of (R)-tertiary leucine:

EXAMPLE 1

5 g (32 mmol) tert. butyl hydantoin are dissolved with 63.1 mg (0.5 mmol) manganese chloride and 63.0 mg (0.5 mmol) sodium sulfite in 1000 ml water, adjusted to pH 8.5 and 50° C., and 1.5 kU (R)-hydantoinase (immobilized, D-Hyd 1) of the Boehringer Mannheim company are added. The conversion is complete after 8 days. The reaction solution is evaporated to 300 ml and the pH adjusted to 0 with concentrated sulfuric acid. Then 2.43 g (xmmol) sodium nitrite in aqueous solution are added in drops within six hours under good agitation. The conversion to tert-leucine is complete after 24 hours. The mixture is adjusted to pH 7 and freed of salts by ion exchange chromatography on strongly acidic resin. The amino acid is eluted by using 5% ammonia, and the ammonia removed by vacuum distillation at 45° C. until the pH is 7.5. 4 g activated carbon is used to clarify for decolorization, the carbon is filtered off and the clarified solution is evaporated to low bulk until dry.

Yield: 3.568 g (85.5% of theory)

EXAMPLE 2

The same procedure is used as in Example 1, but the pH of the reaction with (R) hydantoinase is 9.5. A complete conversion is achieved in four days instead of nine. The matter is decarbamoylized to amino acid as described above and the amino acid product worked off.

Yield: 3.412 g (81.8% of theory)

The proof of identity results from spectroscopic demonstration.

What is claimed is:

1. A method of producing (R)-tertiary leucine, wherein tertiary butyl hydantoin is reacted with an (R)-hydantoinase to produce N-carbamoyl-R-tertiary leucine, the N-carbamoyl-R-tertiary leucine is further reacted to (R)- tertiary leucine either by another enzyme reaction with carbamoylase or by compounding with nitrite.

2. The method according to claim 1, wherein an (R)-hydantoinase from *Escherichia coli* is used.

3. The method according to claim 1 wherein the hydantoinase is present in immobilized form.

4. The method according to claim 1, wherein pH of the reaction is between 7.5 and 10.5.

5. The method according to claim 1, wherein temperature of the reaction is between 25° C. and 60° C.

6. The method according to claim 4, wherein the pH of the reaction is between 8.5 and 10.

7. The method according to claim 5, wherein the temperature of the reaction is between 40° C. and 50° C.

* * * * *